United States Patent [19]

Fabry et al.

[11] Patent Number: 5,322,957
[45] Date of Patent: Jun. 21, 1994

[54] PROCESS FOR THE PRODUCTION OF PARTIAL GLYCERIDE SULFATES

[75] Inventors: Bernd Fabry, Korschenbroich; Uwe Ploog, Haan; Ansgar Behler, Bottrop; Dieter Feustel, Monheim, all of Fed. Rep. of Germany

[73] Assignee: Henkel Kommanditgesellschaft auf Aktien, Duesseldorf, Fed. Rep. of Germany

[21] Appl. No.: 70,315
[22] PCT Filed: Nov. 25, 1991
[86] PCT No.: PCT/EP91/02211
§ 371 Date: Jun. 2, 1993
§ 102(e) Date: Jun. 2, 1993
[87] PCT Pub. No.: WO92/09570
PCT Pub. Date: Jun. 11, 1992

[30] Foreign Application Priority Data
Dec. 3, 1990 [DE] Fed. Rep. of Germany ....... 4038478

[51] Int. Cl.$^5$ ............................................. C07C 409/44
[52] U.S. Cl. ........................................ 558/23; 558/20; 558/24; 558/26; 558/31; 558/32; 558/36; 558/39; 558/40
[58] Field of Search ................ 558/20, 23, 24, 26, 558/31, 32, 36, 39, 40

[56] References Cited

U.S. PATENT DOCUMENTS

| | | | |
|---|---|---|---|
| 2,285,773 | 6/1942 | Harris | 260/400 |
| 2,693,479 | 11/1954 | Ross | 260/400 |
| 2,979,521 | 4/1961 | Gray | 260/458 |
| 3,634,287 | 1/1972 | Woo | 252/353 |

FOREIGN PATENT DOCUMENTS

| | | |
|---|---|---|
| 0267518 | 5/1988 | European Pat. Off. |
| 3821446 | 1/1989 | Fed. Rep. of Germany |
| 7570322 | 10/1973 | Japan |
| 7877014 | 12/1976 | Japan |

OTHER PUBLICATIONS

Anionic Surfactants, Pt.I, Surfactant Science Series vol. 7, W. M. Linfield (Ed.), Marcel Dekker Inc., New York, 1976, p. 219.
Lipidos 26, 19 (1966).
J. Falbe (ed.), "Surfactants in Consumer Products", Springer Verlag, Berlin–Heidelberg, 1987, p. 61.
Philipp, J. Sci.: "Sulfated Monoglyceride Detergents for the Philippines", 311 (1965).

Primary Examiner—Johann Richter
Attorney, Agent, or Firm—Ernest G. Szoke; Wayne C. Jaeschke; Henry E. Millson, Jr.

[57] ABSTRACT

Processes for the production of partial glyceride sulfates comprising the steps of:
A) reacting a mixture containing glycerol and at least one triglyceride with gaseous sulfur trioxide to produce at least one acidic reaction product;
B) ageing the at least one acidic reaction product at an elevated temperature; and
C) neutralizing the at least one aged acidic reaction product with an aqueous base in the presence of a buffer.

20 Claims, No Drawings

PROCESS FOR THE PRODUCTION OF PARTIAL GLYCERIDE SULFATES

This invention relates to a process for the production of partial glyceride sulfates by reaction of mixtures consisting of triglycerides and glycerol with gaseous sulfur trioxide and subsequent neutralization of the reaction products with aqueous bases.

Sulfated partial glycerides, particularly monoglyceride sulfates, are anionic surfactants which are distinguished by high foaming power, good cleaning performance and excellent dermatological compatibility (Anionic Surfactants, Pt. I, Surfactant Science Series, Vol. 7, W.M. Linfield (Ed.), Marcel Dekker Inc., New York, 1976, page 219).

Monoglyceride sulfates are normally produced from glycerol which is first reacted with oleum (US 2,693,479) or chlorosulfonic acid (JP 78/77014) to form glycerol sulfate and then transesterified in the presence of a triglyceride to form the monoglyceride sulfate (Lipidos 26, 19 (1966)). In addition, German patent application DE-A-38 21 446 discloses a process for the production of monoglyceride sulfates by reaction of glycerol with chlorosulfonic acid in an organic solvent, in which fatty acids or fatty acid esters are used for the transesterification. However, sulfonation with oleum or chlorosulfonic acid gives products of high electrolyte content and, accordingly, is not advantageous.

It is known from Philipp. J. Sci. 311 (1965) that mixtures of triglyerides and glycerol can be transesterified in the presence of alkaline catalysts. In addition, it is proposed in the document in question to sulfate the glycerol fatty acid partial esters obtained with sulfuric acid or oleum.

The sulfation of glycerol with sulfur trioxide and subsequent transesterification of the glycerol sulfate formed with triglycerides is known from U.S. Pat. No. 2,979,521. However, products having unsatisfactory degrees of sulfonation are obtained in this way.

In addition, processes for the production of partial glyceride sulfates which start out from monoglycerides are known, for example from U.S. Pat. No. 3,634,287 and from EP-A-O 0 267 518. However, partial glycerides, such as monoglycerides for example, are highly refined products, i.e. their production involves considerable time and energy, so that for economic reasons they are of only limited use for the production of partial glyceride sulfates.

Accordingly, the problem addressed by the present invention was to provide a process for the production of partial glyceride sulfates which would be free from the disadvantages mentioned above.

The present invention relates to a process for the production of partial glyceride sulfates by sulfonation of mixtures consisting of triglycerides and glycerol, characterized in that
a) mixtures consisting of triglycerides and glycerol are reacted with gaseous sulfur trioxide,
b) the acidic reaction products are subjected to ageing at elevated temperature after sulfonation and
c) are subsequently neutralized with aqueous bases in the presence of a buffer.

The invention is based on the observation that, by ageing the crude sulfonation products and using buffers in the neutralization step, partial glyceride sulfates are obtained in high yields even when raw materials in a low state of refinement are used.

The triglycerides used as starting materials for the production of the partial glyceride sulfates in accordance with the invention are natural or synthetic full esters of glycerol with aliphatic carboxylic acids containing 6 to 22 carbon atoms and 0, 1, 2 or 3 double bonds. More particularly, the triglycerides of caproic acid, caprylic acid, capric acid, lauric acid, myristic acid, palmitic acid, palmitoleic acid, stearic acid, oleic acid, elaidic acid, petroselic acid, linoleic acid, linolenic acid, arachic acid, gadoleic acid, behenic acid or erucic acid are suitable for use in accordance with the invention. It is preferred to use glycerol trilaurate.

As usual in oleochemistry, the fatty acid components of the triglycerides may represent technical mixtures such as are typically encountered in natural fats and oils, for example in coconut oil, palm oil, rapeseed oil, sunflower oil, coriander oil or beef tallow. It is preferred to use hydrogenated or unhydrogenated palm kernel oil or coconut oil.

The triglycerides are used in admixture with glycerol for the sulfonation reaction, transesterification and sulfation taking place at the same time. The molar ratio of the mixtures of triglycerides and glycerol may be 1:1 to 1:4. For the selective production of monoglyceride sulfates, it is of advantage to use a ratio of 1:2 to 1:3.

The sulfonation of the mixtures consisting of triglycerides and glycerol with gaseous sulfur trioxide may be carried out by the known method for fatty acid lower alkyl esters (J. Falbe (ed.), "Surfactants in Consumer Products", Springer Verlag, Berlin-Heidelberg, 1987, page 61), preferably using reactors operating on the falling-film principle. The sulfur trioxide is diluted with an inert gas, preferably air or nitrogen, and used in the form of a gas mixture which contains the sulfonating agent in a concentration of 1 to 8% by volume and, more particularly, 2 to 5% by volume.

The sulfonation may be carried out with a molar ratio of partial ester to sulfur trioxide of 1:0.95 to 1:2.2. To obtain light-colored products, it has proved to be optimal to carry out the sulfonation with a corresponding molar ratio of 1:0.95 to 1:1.5. By contrast, to obtain products having a high degree of sulfonation, it is advisable to use a molar ratio of 1:1.51 to 1:2.2.

The sulfonation may be carried out at temperatures of 70° to 98° C. To produce products having a high degree of sulfonation, it has proved to be optimal to select a temperature of 90° to 95° C.

After sulfonation, the crude sulfonation product is subjected to ageing. This step may be carried out continuously, for example in a tube coil, or discontinuously, for example in a tank reactor. The ageing step may be carried out over a period of 1 to 240 minutes and preferably over a period of 5 to 30 minutes at temperatures of 70° to 98° C. and preferably at temperatures of 90° to 95° C. If ageing is carried out at low temperatures within the limits indicated, long residence times are necessary to obtain high degrees of sulfonation and vice versa.

After ageing, the acidic sulfonation products formed during the sulfonation reaction are stirred together with aqueous bases into an aqueous buffer solution and neutralized, a pH value of 5.5 to 9 and preferably 6.5 to 8 having to be maintained because otherwise the ester bond would be hydrolyzed or the sulfate group would be eliminated. Suitable buffers are, for example, 1 to 5% by weight aqueous solutions of sodium triphosphate, sodium hydrogen carbonate or citric acid.

Suitable bases for the neutralization step are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di-and tri-$C_{2-4}$-alkanolamines, for example mono-, di- and triethanolamine, and also primary, secondary or tertiary $C_{1-4}$ alkyl amines. The neutralization bases are preferably used in the form of 5 to 55% by weight aqueous solutions, 5 to 25% by weight aqueous sodium hydroxide solutions being preferred.

The sulfonation products are complex mixtures essentially containing sulfation products of the primary and secondary hydroxyl groups of the partial glycerides formed by transesterification from the triglycerides. In addition, the reaction mixture may contain open-chain and cyclic glycerol sulfates and also alpha-glycerol ester sulfonates, soaps, sulfonated soaps and glycerol. Where unsaturated triglycerides are used as starting materials, an addition of the sulfur trioxide onto the double bond of the fatty acid component also takes place to a minor extent with formation of internal glycerol ester sulfonates.

After neutralization, the sulfonation products may be bleached in known manner by addition of hydrogen peroxide or sodium hypochlorite solution. Based on the solids content of the solution of sulfonation products, 0.2 to 2% by weight hydrogen peroxide, expressed as 100% substance, or corresponding quantities of sodium hypochlorite are used. In addition, it is advisable to add a preservative, for example formaldehyde solution, p-hydroxybenzoate, sorbic acid or any other known preservative, for stabilization against bacterial contamination.

The partial glyceride sulfates have surface-active properties and are suitable for the production of powder-form or liquid detergents and cleaning products and also hair-care and personal hygiene products.

The following Examples are intended to illustrate the invention without limiting it in any way.

EXAMPLES

Examples 1 to 7

General procedure for the sulfonation of triglyceride/glycerol mixtures

A mixture of 673 g (1 mol) hydrogenated palm kernel oil (saponification value 250, iodine value 0.9) and 215 g (2.2 mol) glycerol was introduced into a 1 liter sulfonation reactor with jacket cooling and a gas inlet pipe and reacted with 80 to 176 g (1.0 to 2.2) gaseous sulfur trioxide. To this end, the $SO_3$ was driven out from a corresponding quantity of 65% by weight oleum, diluted with nitrogen to a concentration of 5% by volume and introduced into the reaction mixture over a period t of 60 to 90 minutes at a temperature T of 80 to 95° C. The acidic sulfonation product was then subjected to ageing and, to this end, was stored for 30 minutes at 90° C. It was then stirred together with 25% by weight sodium hydroxide solution into 200 ml of a 1% by weight solution of sodium triphosphate and neutralized at pH 6.5 to 8. The reaction conditions and characteristic data of the products are set out in Table 1.

Example 8

Continuous sulfonation of coconut oil and glycerol

In a continuously operating falling-film reactor (length 120 cm, cross-section 1 cm, educt throughput 600 g/h) with jacket cooling and a side inlet for gaseous $SO_3$, a mixture of 3300 g (5 mol) technical hydrogenated coconut oil (saponification value 255, iodine value 0.9) and 1012 g (11 mol) glycerol were reacted with 600 g (5 mol) sulfur trioxide at 95° C. The sulfur trioxide was driven out by heating from a corresponding quantity of 65% by weight oleum, diluted with nitrogen to a concentration of 5% by volume and contacted with the monoglyceride film via a nozzle. The crude sulfonation product was then subjected to ageing and, to this end, was stored for 30 minutes at 90° C. It was then stirred together with 25% by weight sodium hydroxide solution into 200 ml of a 1% by weight solution of sodium triphosphate and neutralized at pH 6.5 to 8. The characteristic data of the reaction product are set out in Table 1.

Comparison Example 1

Palm kernel oil, glycerol and sulfur trioxide were reacted at a temperature of 40° C. as in Example 5. The characteristic data of the product are set out in Table 1.

Comparison Example 2

Palm kernel oil, glycerol and sulfur trioxide were reacted at a temperature of 95° C. as in Example 5. The acidic sulfonation product was neutralized with 40% by weight aqueous sodium hydroxide solution in the absence of the sodium phosphate buffer. The characteristic data of the product are set out in Table 1.

The content of glyceride sulfates (WAS) and the unsulfonated components of the starting product (US) were determined in accordance with DGF-Einheitsmethoden, Stuttgart, 1950–1984, H-III-10 and G-II-6b. The glycerol sulfate content was determined by ion chromatography while the sulfate content was determined by potentiometry and expressed as sodium sulfate. The water content was determined by the Fischer method. Glycerol was enzymatically determined while the soap content was determined by thin layer chromatography.

TABLE 1

Sulfonation of triglyceride/glycerol mixtures
Percentages as % by weight

| Ex. | E:$SO_3$ | T °C. | t mins. | GIS % | Gls % | Gl. % | Gly % | Soap % | $SO_4^{2-}$ % | $H_2O$ % |
|---|---|---|---|---|---|---|---|---|---|---|
| 1 | 1:1.0 | 95 | 60 | 5.9 | 2.3 | 9.0 | 1.5 | 1.9 | 1.1 | 78.3 |
| 2 | 1:1.2 | 95 | 65 | 6.6 | 2.5 | 8.4 | 0.3 | 2.1 | 1.5 | 78.6 |
| 3 | 1:1.5 | 95 | 70 | 7.1 | 2.7 | 7.7 | 0.2 | 2.3 | 1.7 | 78.5 |
| 4 | 1:1.8 | 80 | 80 | 7.4 | 2.8 | 7.4 | 2.1 | 2.5 | 2.0 | 75.9 |
| 5 | 1:1.8 | 95 | 80 | 8.5 | 3.0 | 6.5 | 0.1 | 3.1 | 2.1 | 76.7 |
| 6 | 1:2.0 | 95 | 80 | 9.1 | 3.1 | 6.1 | 0.1 | 3.3 | 2.4 | 76.0 |
| 7 | 1:2.2 | 95 | 85 | 9.8 | 3.2 | 5.4 | 0.0 | 3.7 | 2.8 | 75.1 |
| 8 | 1:1.5 | 95 | — | 7.6 | 2.5 | 6.9 | 0.2 | 2.3 | 1.7 | 78.5 |
| C1 | 1:1.8 | 40 | 80 | 2.6 | 0.9 | 12.5 | 3.3 | 0.9 | 3.7 | 76.1 |

TABLE 1-continued

| | | Sulfonation of triglyceride/glycerol mixtures Percentages as % by weight | | | | | | | | |
|---|---|---|---|---|---|---|---|---|---|---|
| Ex. | E:SO$_3$ | T °C. | t mins. | GlS % | Gls % | Gl. % | Gly % | Soap % | SO$_4^{2-}$ % | H$_2$O % |
| C2 | 1:1.8 | 95 | 80 | 6.5 | 2.1 | 6.1 | 0.1 | 5.4 | 2.1 | 77.7 |

Legend:
E:SO$_3$ = Molar ratio of starting material to SO$_3$
GlS = Fatty acid glyceride sulfates
Gls = Glycerol sulfates
Gl = Unsulfonated components of the hydro-genated palm kernel oil
Gly = Free glycerol

We claim:

1. A process for the production of partial glyceride sulfates comprising the steps of
  A) reacting a mixture containing glycerol and at least one triglyceride with gaseous sulfur trioxide to produce at least one acidic reaction product;
  B) ageing the at least one acidic reaction product at an elevated temperature; and
  C) neutralizing the at least one aged acidic reaction product with an aqueous base in the presence of a buffer.

2. The process of claim 1 wherein in step A) the at least one triglyceride is a natural or synthetic full ester of glycerol with aliphatic carboxylic acids containing 6 to 22 carbon atoms and 0, 1, 2, or 3 double bonds.

3. The process of claim 2 wherein the at least one triglyceride is a technical mixture from a natural fat or oil.

4. The process of claim 2 wherein the at least one triglyceride is hydrogenated or unhydrogenated palm kernel oil or coconut oil.

5. The process of claim 1 wherein step A) is carried out in a continuously operated falling-film reactor.

6. The process of claim 1 wherein in step A) the molar ratio of triglyceride to glycerol is from 1:1 to 1:4.

7. The process of claim 6 wherein said molar ratio is from 1:2 to 1:3.

8. The process of claim 1 wherein step A) is carried out at a temperature in the range of from 70° to 98° C.

9. The process of claim 8 wherein said temperature is in the range of from 90° to 95° C.

10. The process of claim 1 wherein in step A) the molar ratio of triglyceride to sulfur trioxide is from 1:0.95 to 1:1.5.

11. The process of claim 10 wherein said molar ratio is from 1:1.51 to 1:2.2.

12. The process of claim 1 wherein step B) is carried out at a temperature of from 70° to 98° C.

13. The process of claim 12 wherein step B) is carried out at a temperature of from 90° to 95° C.

14. The process of claim 1 wherein step B) is carried out for a period of from 1 to 240 minutes.

15. The process of claim 14 wherein said period is from 5 to 30 minutes.

16. The process of claim 1 wherein the aqueous base in step C) is selected from the group consisting of alkali metal hydroxides, alkaline earth metal oxides and hydroxides, ammonia, mono-, di- and tri-C$_{2-4}$-alkanolamines, and primary, secondary and tertiary C$_{1-4}$ alkyl amines, and the aqueous base contains from 5 to 55% by weight of base.

17. The process of claim 1 wherein step C) is carried out at a ph of from 5.5 to 9.

18. The process of claim 1 wherein in step A) the at least one triglyceride is a natural or synthetic full ester of glycerol with aliphatic carboxylic acids containing 6 to 22 carbon atoms and 0, 1, 2, or 3 double bonds, the molar ratio of triglyceride to glycerol is from 1:1 to 1:4, the molar ratio of triglyceride to sulfur trioxide is from 1:0.95 to 1:1.5, step A) is carried out at a temperature in the range of from 70° to 98° C.; step B) is carried out at a temperature of from 70° to 98° C. and for a period of from 1 to 240 minutes; and step C) is carried out at a pH of from 5.5 to 9.

19. The process of claim 18 wherein step A) is carried out in a continuously operated falling-film reactor at a temperature of from 90° to 95° C.; step B) is carried out at a temperature in the range of from 90° to 95° C. for a period of from 5 to 30 minutes; and the aqueous base in step C) contains from 5 to 55% by weight of a base selected from the group consisting of alkali metal hydroxides, alkaline earth metal oxides and hydroxides, ammonia, mono-, di- and tri-C$_{2-4}$-alkanolamines, and primary, secondary and tertiary C$_{1-4}$ alkyl amines, and the pH in step C) is from 6.5 to 8.

20. The process of claim 19 wherein in step A) the molar ratio of triglyceride to glycerol is from 1:2 to 1:3 and the molar ratio of triglyceride to sulfur trioxide is from 1:1.51 to 1:2.2.

* * * * *